United States Patent [19]
Weisrock et al.

[11] 4,418,145
[45] Nov. 29, 1983

[54] *XANTHOMONAS CAMPESTRIS* ATCC 31601 AND PROCESS FOR USE

[75] Inventors: William P. Weisrock, Tulsa, Okla.; Edward F. McCarthy, Naperville, Ill.

[73] Assignee: Standard Oil Company, Chicago, Ill.

[21] Appl. No.: 167,870

[22] Filed: Jul. 14, 1980

[51] Int. Cl.[3] ........................ C12P 19/06; C12N 1/20; C12R 1/64

[52] U.S. Cl. .................................... 435/104; 435/253; 435/910

[58] Field of Search ................................ 435/104, 910

[56] References Cited

U.S. PATENT DOCUMENTS 3,773,752 11/1973 Buchanan et al. .............. 435/104 X

*Primary Examiner*—Lionel M. Shapiro
*Attorney, Agent, or Firm*—Stephen R. May; Fred E. Hook

[57] ABSTRACT

A new degenerative-resistant strain of *Xanthomonas campestris* is described which is suitable for long-term continuous fermentation to produce xanthan gum from a nutrient medium, typically containing inorganic salts, glucose, $NH_4Cl$, and citric acid, with or without yeast extract or yeast autolysate.

14 Claims, No Drawings

XANTHOMONAS CAMPESTRIS ATCC 31601 AND PROCESS FOR USE

INTRODUCTION

The present invention relates to the production of heteropolysaccharides by the action of certain novel degenerative resistant strains of *Xanthomonas campestris* on aqueous nutrient media. More particularly, it is concerned with the production of xanthan gum by the use of these novel bacteria.

BACKGROUND

Batch fermentation of an inoculated medium with *Xanthomonas campestris* NRRL B-1459 for 36-72 hours under aerobic conditions results in the formation of xanthan gum, which is separated from the other components of the medium by precipitation with acetone or methanol in a known manner. Because of time required to ferment each batch, the low biopolymer content of the fermented medium and the processing required for the recovery and purification of the product, xanthan gum produced by batch fermentation, hereinafter also referred to as xanthan, is relatively expensive.

Because continuous operation of a fermentation process offers a number of potential advantages over conventional batch methods that could be reflected in lower costs, considerable effort has been put forth in the past to perfect conditions that would support a reliable continuous process. But even with a continuous process a cheap medium from which xanthan can be produced is required. In addition to the necessity of an inexpensive medium in the manufacture of a low cost xanthan product, the ratio of xanthan to cells (bacteria) should be as high as possible in order to reduce subsequent filtration costs for cell removal. The specific productivity of the culture employed also should be as high as possible in order to maintain the aforesaid high ratio as well as to reduce vessel volume and capital costs. The expression "specific productivity" as used in the present description is intended to mean the number of grams of xanthan produced/grams of cells/hour. The culture should be stable under continuous culture conditions on a long term basis to avoid frequent restarts and lost productivity.

Although xanthan has been produced by continuous fermentation in the past, such methods have not met with unqualified success. In some cases, vitamins and/or amino acids had to be employed in the medium in substantial quantities in order to avoid culture degeneration or to improve specific productivity. Use of these additives, as well as soybean protein, cotton seed protein, etc., all tend to make the xanthan thus produced more costly.

It is well known that the continuous production of xanthan by the use of *Xanthomonas campestris* B-1459 has been hampered by a tendency of the culture to change or degenerate after a fairly small and specific number of turnovers, the time required during the fermentation to completely replace one volume of broth in the fermentation vessel. Normally, 6-9 turnovers are the maximum that can be obtained before degeneration of the culture occurs. At the same time, there is a decrease in viscosity, a loss in volumetric productivity of xanthan gum, i.e., grams of xanthan/liter of broth/hour, and appearance of a variety of culture variants or strains that no longer produce xanthan or else produce a xanthan of low quality. It has been demonstrated that culture degeneration occurs when dried distillers solubles (DDS) is used in the nutrient medium as the complex nitrogen source, whether in the whole form or as a water soluble extract. In other cases, certain strains of Xanthomonas have been grown successfully without culture degeneration in simple minimal media, but the xanthan:cell ratio and specific productivity have been low, on the order of 0.1-0.12 gm xanthan/gm of cells/hr.

Earlier work has indicated that heteropolysaccharides produced by the action of Xanthomonas bacteria on assimilable carbohydrate containing media have potential applications as film forming agents, as thickeners for body building agents in edible products, cosmetic preparations, pharmaceutical vehicles, oil field drilling fluids, fracturing liquids and similar compositions and as emulsifying, stabilizing and sizing agents. Heteropolysaccharides, particularly xanthan gum, have significant potential as a mobility control agent in micellar polymer flooding. This gum has excellent viscosifying properties at low concentration, is resistant to shear degradation and exhibits only minimal losses in viscosity as a function of temperature, pH and ionic strength. For these reasons, xanthan gum is an attractive alternative to synthetic polyacrylamides for enhanced oil recovery operations.

SUMMARY OF THE INVENTION

We have now discovered a degenerative-resistant strain of *Xanthomonas campestris* and have developed a process for using this strain to effectively overcome the problems of continuous xanthan production recited above. This strain of *Xanthomonas campestris* which we have designated *Xanthomonas campestris* XCP-19 ATCC 31601 is capable of continuously producing xanthan at high specific productivities, i.e., 0.24 to 0.32 gm xanthan/gm cells/hr, for several hundred hours without culture degeneration from inexpensive aqueous nutrient media such as, for example, a minimal medium consisting primarily of inorganic salts, glucose and $NH_4Cl$. The medium may or may not also contain a yeast extract or yeast autolysate as a supplemental nitrogen source. Generally, it may be said that any medium having assimilable sources of carbon, nitrogen and inorganic substances will serve satisfactorily for use with this new organism.

The process of our invention in which this new strain is utilized can be either a single stage or two-stage continuous fermentation process. In the single stage embodiment the organism is grown, preferably under conditions such that the quantity of one of the growth nutrients present is limited. The quantity of biomass obtained will be determined by the concentration of the limiting nutrient. A portion of the residual glucose or equivalent sugar present is converted to xanthan gum and the latter ultimately recovered from the fermentation effluent. In the two-stage process, the aforesaid fermenter effluent is taken to a second fermentation stage where additional glucose or equivalent sugar is introduced and converted to xanthan. In operation of the second stage, a balance of the flow of the first stage effluent and glucose solution must approximate the flow rate of the second stage effluent. The growth limiting nutrients normally employed are nitrogen, phosphorous or sulfur.

SPECIFIC EMBODIMENTS OF THE INVENTION

Subcultures of this living organism can be obtained upon request from the permanent collection of the American Type Culture Collection, 12301 Parklawn Drive, Rockville, MD 20852. The accession number in this repository for *Xanthomonas campestris* XCP-19 is given above. The novel *Xanthomonas campestris* strain referred to was isolated from a pilot plant run in which a 28 liter fermenter was operated using a culture of *Xanthomonas campestris* NRRL B1459, growing in a suitable nutrient medium having a composition as shown in Table I.

TABLE I

| Component | Concentration (ppm) |
|---|---|
| Glucose | 22,000 |
| NH$_4$Cl | 300 as N |
| KOH | 1000 + as K |
| H$_3$PO$_4$ | 300 as P |
| MgSO$_4$ | 100 as Mg |
| CaCl$_2$ | 10 as Ca |
| NaCl | 10 as Na |
| FeSO$_4$ | 2 as Fe |
| ZnSO$_4$ | 0.35 as Zn |
| MnSO$_4$ | 0.35 as Mn |
| Na$_2$MoO$_4$ | 0.21 as Mo |
| H$_3$BO$_3$ | 0.07 as B |
| KI | 0.14 as I |
| CuSO$_4$ | 0.020 as Cu |
| Citric Acid | 250 |

Continuous fermentation of the above medium was initially conducted at 28° C., a pH of 6.8, an aeration rate of 0.2-0.4 vol./vol./min., agitation rate of 230 rpm, dissolved oxygen of 90% saturation, and a dilution rate of 0.08 hr$^{-1}$. After about 6 turnovers, the culture began to degenerate with lowered xanthan productivity and viscosity. At this point, several changes were made to the medium. The pH was lowered to 6.4 from 6.8; iron, copper and zinc concentrations in the broth were raised to 3, 0.6 and 1 ppm, respectively, by adding these trace elements to the glucose feed tank (they were previously added with the rest of the inorganic salts), the citric acid level was doubled to 500 ppm, and H$_3$PO$_4$ and MgSO$_4$ levels were reduced by half. For 2 to 3 culture turnovers after these changes the culture continued to degenerate with viscosity dropping to 70 cp and specific productivity decreasing to 0.07 gm/gm cells/hr.

During an overnight period, the exit line, from the fermenter plugged and the culture went into a semibatch/low dilution rate condition for about 10 hours. The following morning, viscosity was up to 300 cp and when level and flow rates were corrected, it continued to increase. For the next 10 turnovers, specific productivity gradually increased to over 0.35 gm xanthan/gm cells/hr, and culture morphology became normal again. The culture was maintained at this high productivity for some 30 turnovers after recovery without any evidence of culture degeneration before being terminated by a pH upset. This highly productive culture was saved in a viable state and used to isolate the novel *Xanthomonas campestris* strain referred to above.

After standard plate counts were made on the culture, using YM agar (Difco), 9 isolated colonies of varying sizes were picked and subcultured on YM agar for purification. Three isolates were discarded as obvious duplicates, and the remaining six isolates P-101, P-102, P-104, P-105, P-107 and P-108 were maintained for three bi-weekly transfers on YM agar slants. The isolates were then subcultured to EMSY-1 broth and then maintained on EMSY-1 agar slants as well as on the YM agar slants. In addition, cultures grown in EMSY-1 broth were frozen in liquid nitrogen. The composition of this (EMSY-1) broth is given in Table II.

TABLE II

| Component | Concentration (ppm) |
|---|---|
| Glucose | 10,000 |
| NH$_4$Cl | 112 as N |
| KH$_2$PO$_4$ | 386 as P |
| Na$_2$HPO$_4$ | 390 as P |
| MgSO$_4$.7H$_2$O | 40 as Mg |
| CaCl$_2$.2H$_2$O | 10 as Ca |
| NaCl | 10 as Na |
| FeCl.6H$_2$O | 1 as Fe |
| ZnSO$_4$.7H$_2$O | 0.33 as Zn |
| MnSO$_4$.H$_2$O | 0.1 as Mn |
| Na$_2$MoO$_4$.2H$_2$O | 0.067 as Mo |
| H$_3$BO$_3$ | 0.033 as B |
| KI | 0.033 as I |
| CuSO$_4$.5H$_2$O | 0.2 as Cu |
| Citric Acid | 500 |
| Yeast Extract | 400 |

The *Xanthomonas campestris* XCP-1 strain was obtained by pooling five of the six remaining isolates, i.e., P-101, P-102, P-104, P-105, and P-108, into one culture. The XCP-19 strain was obtained from the XCP-1 culture, after several transfers, as a single large (4 mm) light yellow colony and this isolate was propagated separately.

STRAIN DESCRIPTIONS

The above-mentioned strain of *Xanthomonas campestris* was characterized with respect to to *Xanthomonas campestris* strain NRRL B-1459 from which strain XCP-19 was originally derived. The following descriptions characterize the strain XCP-19 ATCC 31601.

I. Cell Morphology

A. After growth in EMSY-1 broth for 18 hours at 28° C., cells appear singly and in pairs with infrequent chains of 3 or 4 cells also occurring. Cell dimensions are 0.3-0.6 microns in width by 0.5-1.5 microns in length. Often cells in pairs appear almost coccoid.

B. After growth in YM broth (Difco) for 18 hours at 28° C., cells appear singly or in pairs, with chains of 3-4 cells. Chaining is more abundant than in EMSY-1 broth. Cell dimensions are larger than in EMSY-1 broth, being 0.5-0.7 microns in width and 0.75-3 microns in length.

C. Strain XCP-19 does not exhibit motility, has a negative Gram stain reaction, and does not form endospores. These bacteria may be reproduced only asexually by means of binary fission.

II. Colony Morphology

A. After 72 hours growth at 28° C. on EMSY-1 agar plates, isolated colonies are pale cream in color, circular, entire, mucoid, and raised. Colony diameter is 2-3 mm.

B. After 72 hours growth at 28° C. on YM agar (Difco) isolated colonies are whitish to creamy in color, circular, entire, mucoid, and raised. Typical colony diameter is 3-4 mm.

C. After 72 hours growth at 28° C. on Nutrient Agar (Difco) containing 1% dextrose, isolated colonies are pale yellow in color, circular, entire, mucoid, and raised. Colony diameter is about 0.5-2 mm.

III. Biochemical Characteristics

In order to determine whether strain XCP-19 is physiologically different from *Xanthomonas campestris* NRRL B-1459, the following tests were conducted.

A. Growth at 35° C. Inoculated slants of YM agar (Difco) and EMSY-1 agar (see Table II for composition) were incubated at 35° C. for five days and the results are shown in Table III.

TABLE III*

| Strain No. | YM Agar | EMSY-1 Agar |
|---|---|---|
| XCP-19 | 0 | 0 |
| B-1459 | 2+ | 0 |

*0 = no growth; 1+ = slight growth; 4+ = heavy growth

B. Growth Characteristics in Minimal Medium. Inoculated tubes of liquid EMS-2 medium shown in Table IV were incubated at 28° C. for 96 hours.

TABLE IV

| Component | Concentration (ppm) |
|---|---|
| Glucose | 22,500 |
| $NH_4Cl$ | 224 as N |
| $KH_2PO_4$ | 150 as P |
| $MgSO_4.7H_2O$ | 40 as Mg |
| $CaCl_2.2H_2O$ | 10 as Ca |
| Citric Acid | 500 |
| $FeCl_3.6H_2O$ | 2 as Fe |
| $ZnSO_4.7H_2O$ | 0.66 as Zn |
| $CuSO_4.5H_2O$ | 0.4 as Cu |
| $MnSO_4.H_2O$ | 0.2 as Mn |
| $Na_2MoO_4.2H_2O$ | 0.13 as Mo |
| $H_3BO_3$ | 0.066 as B |
| KI | 0.066 as I |
| NaCl | 10 as Na |

Strain XCP-19 showed heavy growth throughout the tubes with a ragged surface pellicle and clumping in the broth. Strain B-1459 showed less growth overall and only a slight surface growth.

C. Hydrolysis of Gelatin, Casein, and Starch. Solid agar media individually containing 0.4% gelatin, 0.4% casein, or 0.3% soluble starch were prepared and used according to the procedure in "Identification Methods for Microbiologists", 1966, B. M. Gibbs and F. A. Skinner, eds., Academic Press, p. 12.

TABLE V

| Strain No. | Gelatin | Casein | Starch |
|---|---|---|---|
| XCP-19 | 4+ | 2+ | 4+ |
| B-1459 | 4+ | 4+ | 4+ |

As shown in Table V, strain B-1459 showed complete hydrolysis of all three substrates, whereas XCP-19 showed lesser degrees of hydrolysis of casein.

D. Action on Litmus Milk. Cultures inoculated into Litmus Milk medium (Difco) were incubated at 28° C. for three weeks, according to the method of Ivanoff et. al. (1938, J. Bacteriol. 35 235). Strains XCP-19 and B-1459 were both active on litmus milk with peptonization, litmus reduction, and precipitate formation.

E. Hydrogen Sulfide Production. The medium for $H_2S$ production was prepared according to the method of Hayward and Hotchkiss (1961, J. Gen. Microbiol. 26, 133–140). $H_2S$ production was determined by the use of lead acetate paper strips suspended over the medium in loosely capped tubes. The cultures were incubated for six days at 28° C. and observed for blackening of the strips. Each of the strains produced hydrogen sulfide.

F. Urease Production. Urea medium was prepared according to the method of Christensen (1946, J. Bacteriol. 52 461–466). The slants were inoculated and incubated at 28° C. for 14 days. A red to violet color in the medium would be indicative of urea hydrolysis. Urease production was found to be negative for each of the strains tested.

G. Growth in Presence of Salt. Basal media containing NaCl at concentrations of 1, 2, 3, 4, and 5% were prepared according to the method of Hayward and Hotchkiss (1961. J. Gen. Microbiol. 26 133–140). Cultures were inoculated and incubated at 28° C. for 14 days. Both strains tested gave an identical growth pattern as shown in Table VI.

TABLE VI

| Strain No. | Salt Conc'n | | | | |
| | 1% | 2% | 3% | 4% | 5% |
|---|---|---|---|---|---|
| XCP-19 | 4+ | 3+ | 3+ | 2+ | 0 |
| B-1459 | 4+ | 3+ | 3+ | 2+ | 0 |

H. Carbohydrate Assimilation Pattern. A basal carbohydrate assimilation medium was prepared according to the method of Hayward and Hotchkiss (1961. J. Gen. Microbiol. 26 133–140). Each strain was inoculated into replicate tubes containing the carbohydrates shown in Table VII and incubated for 14 days at 28° C.

TABLE VII

| Carbohydrate | XCP-19 | B-1459 |
|---|---|---|
| Glucose | + | + |
| Galactose | + | + |
| Arabinose | + | + |
| Mannose | + | + |
| Melibiose | + | + |
| Cellobiose | + | + |
| Sucrose | weak | weak |
| Fructose | weak | weak |
| Trehalose | + | + |
| Xylose | − | − |
| Mannitol | + | + |
| Lactose | − | − |
| Maltose | + | + |

As can be seen in Table VII, both strains gave an identical assimilation profile.

I. Oxidase Production. Using isolated colonies from 72 hour old YM agar (Difco) plates, the strains were tested for presence of indophenol oxidase using the method of Gaby and Hadley (1957. J. Bacteriol. 74 356–358). Each strain was positive for oxidase.

J. Catalase Production. Growth from a 48 hour YM agar (Difco) slant was tested for catalase activity by emulsifying a loopful of culture in a drop of 3% $H_2O_2$ and observing for effervescence. Strains XCP-19 and B-1459 were weakly positive.

K. Utilization of Organic Acids. EMS-2 basal medium without glucose was prepared. Replicate tubes containing 1% citric, malic, succinic, benzoic, and tartaric acids were inoculated and incubated at 28° C. for 14 days and observed for extent of growth. As shown by the results given in Table VIII, both strains were identical except that XCP-19 gave slightly less growth on citric acid.

TABLE VIII

| Organic Acid | XCP-19 | B-1459 |
|---|---|---|
| Citrate | 2+ | 3+ |
| Malate | 4+ | 4+ |
| Succinate | 4+ | 4+ |

TABLE VIII-continued

| Organic Acid | XCP-19 | B-1459 |
| --- | --- | --- |
| Benzoate | 0 | 0 |
| Tartrate | 1+ | 1+ |

L. Indole Production. The strains were tested for indole production for the same peptone-water medium used to test for H₂S production, following the method of Hayward and Hotchkiss (1961. J. Gen Microbiol. 26 133-140). All strains were negative for indole production.

M. Acetoin Production. The strains were tested for acetoin production using MRVP medium (Difco) after incubation of the inoculated cultures for six days at 28° C., following the method given in the reference in (L) above. Neither strain tested positive for acetoin.

Summary of Characterization Studies

Strain XCP-19 is essentially indistinguishable from $X.$ campestris strain NRRL B-1459 on the basis of cell morphology. However, definite differences in colonial morphology make this strain distinguishable from B-1459.

XCP-19 produces larger, paler yellow colonies than B-1459 on EMSY-1 and Nutrient+Glucose Agar, and almost colorless colonies on YM agar.

In terms of physiological characteristics, this strain is very similar to NRRL B-1459 except that B-1459 grows poorly on a minimal medium. In addition, XCP-19 is distinguishable in that it shows no growth on YM agar at 35° C., exhibits less active casein hydrolysis and gives less growth on citrate.

The foregoing is intended to point out that, while the major distinguishing characteristics of the XCP-19 strain lie in its high xanthan specific productivity and resistance to degeneration in continuous culture, other distinguishing characteristics nevertheless are present.

In carrying out the process of the present invention, the fermenter medium is seeded with an inoculum of culture grown in the same medium as that to be used for fermentation at an inoculum level of 5-10% of the medium volume. The culture is grown in a batch mode for 24-48 hours, until a desired cell concentration is reached (usually 1.5-2.5 gm cells/l). Thereafter, continuous flow of medium is started into the fermenter such that the dilution rate is 75% or less of the specific growth rate at which the organism is growing at that point. Continuous harvesting of a volume of culture broth equal to the volume of medium introduced is also carried out. After approximately two culture turnovers, the dilution rate is adjusted as desired. Xanthan gum, which exists in the recovered broth, can be used without further purification, or filtered to remove cells, or can be precipitated with an alcohol, such as ethyl or isopropyl alcohol, with or without initial cell removal. The medium used in this process is a preferably minimal medium consisting primarily of inorganic salts, NH₄Cl, glucose, and citric acid, with or without additional yeast extract or yeast autolysate.

The term "minimal medium" as used throughout the present description and claims should be interpreted to cover media of the type generally referred to herein and specifically in the Examples, together with modifications apparent to those skilled in this field.

Operating conditions to be employed in the process of our invention include the following:
Agitation: 100-2000 rpm
  Preferably: 500-1000 rpm
Air Rate: 0.1-2 vol./vol./min.
  Preferably: 0.5-1 vol./vol./min.
Temperature: 20°-35° C.
  Preferably: 25°-30° C.
pH: 5-8
  Preferably: 6.4-7.4
Dissolved Oxygen: 10-90% saturation
  Preferably: 20-60% saturation
Dilution Rate: 0.01-0.15 hr⁻¹
  Preferably: 0.04-0.1 hr⁻¹

Our invention will be illustrated by reference to the following specific examples:

EXAMPLE I

This Example shows that when *Xanthomonas campestris* NRRL B-1459, is grown in a minimal medium in continuous culture, the organism exhibits only low specific productivity and degenerates in a short time. The culture was grown in a 28 liter fermenter in a minimal medium having a composition shown in Table IX.

TABLE IX

| Component | Concentration (ppm) |
| --- | --- |
| Glucose | 22,000 |
| NH₄Cl | 300 as N |
| KOH | 1,000 as K |
| H₃PO₄ | 150 as P |
| MgSO₄ | 40 as Mg |
| CaCl₂ | 10 as Ca |
| NaCl | 10 as Na |
| Citric Acid | 500 |
| FeSO₄ | 3 as Fe |
| ZnSO₄ | 1 as Zn |
| MnSO₄ | 0.3 as Mn |
| Na₂MoO₄ | 0.2 as Mo |
| H₃BO₃ | 0.1 as B |
| KI | 0.1 as I |
| CuSO₄ | 0.6 as Cu |

*Xanthomonas campestris* NRRL B-1459 was maintained on YM agar (Difco) slants at 4° C. and transferred to fresh agar slants at bi-weekly intervals. For inoculum preparation, a loopful of culture from a fresh (<3 day old) slant was inoculated into a 16×125 mm tube containing 7 ml of YM broth. The culture was incubated at 28° C. on a rotary shaker at 150 rpm, at a 20° inclination for 18 hours. At this point, the contents of the tube were transferred to 50 ml YM broth in a 500 ml Erlenmeyer flask, and incubated at 28° C. on a rotary shaker at 250 RPM for 18-24 hours. Next, the contents of the flask were transferred to a 2000 ml Fernbach flask containing 700 ml of a mineral salt-glucose-NH₄Cl medium, of the composition given above in Table III. This was incubated under the same conditions as for the 50 ml flask, but for a total of 40 hours. Next, the entire culture was used to inoculate 20 liters of the same medium contained in a 28 liter New Brunswick fermenter (Model CMF-128S). The initial operating conditions employed were as follows:
Temperature—29° C.
pH—6.0
Agitation—230 rpm
Air Rate—0.2-0.4 vol/vol/min
Dissolved O₂—90% saturation After an initial growth lag of about 30 hours, cell growth proceeded over the next 30 hours. When the cell concentration reached 0.9 gm/liter, continuous operation was started at an initial dilution rate of 0.07 hr⁻¹. Within 48 hours, the cell concentration rose to 2.5 gm/liter. After about 10 culture turnovers, the viscosity and specific productivity started to decline and were eventually almost totally lost. Cell morphology became abnormal and gum quality deteriorated badly. All of these changes proved to be irreversible and the culture did not revert to normal. The results obtained in this run are shown in Table X.

The culture of *Xanthomonas campestris* XCP-19 ATCC 31601 was grown for 56 culture turnovers (720 hours) without degeneration under essentially the same conditions as employed in Example I. For the first 24 turnovers, the specific productivity averaged 0.253

TABLE X

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 0–34 | 1.3–1.9 | .26–.30 | 120–340 | .20 | .11–.15 | .07–.08 | 0–2.5 |
| 34–130 | 2.6–2.56 | .32–.39 | 640–850 | .23–.31 | .10–.13 | .07–.085 | 2.5–9.7 |
| 130–178 | 1.7–2.17 | .23–.265 | 420–430 | .17–.22 | .09–.10 | .07–.08 | 9.7–13.7 |
| 178–202 | 1.0 | .187 | 160 | .13 | .13 | .07 | 13.5–15 |
| 202–266 | .6–1.1 | .12–.14 | 28–48 | .1–.11 | .09–.175 | .077 | 15–20.1 |

EXAMPLE II

In this example, *Xanthomonas campestris* XCP-19 ATCC 31601 was grown in continuous culture in a medium (EMS-2) supplemented with 0.04% yeast extract having the following composition:

TABLE XI

| Composition of EMS-2 Medium | |
|---|---|
| Component | Concentration (ppm) |
| $NH_4Cl$ | 224 as N |
| $KH_2PO_4$ | 150 as P |
| $MgSO_4.7H_2O$ | 40 as Mg |
| $CaCl_2.2H_2O$ | 10 as Ca |
| NaCl | 10 as Na |
| Citric Acid | 500 |
| $FeCl_3.6H_2O$ | 2 as Fe |
| $ZnSO_4$ | 0.66 as Zn |
| $MnSO_4$ | 0.2 as Mn |
| $CuSO_4$ | 0.4 as Cu |
| $Na_2MoO_4$ | 0.13 as Mo |
| $H_3BO_3$ | 0.066 as B |
| KI | 0.066 as I |
| Glucose | 22,500 |

For inoculum preparation, a loopful of culture from a fresh (<3 day old) slant was inoculated into a 16×125 mm tube containing 7 ml of EMSY-1 broth. The culture was incubated at 28° C. on a rotary shaker at 150 rpm, at a 20° C. inclination for 18 hours. At this point, the contents of the tube were transferred to 50 ml EMS-2 broth (containing 0.04% YE (see Table XI) in a 500 ml Erlenmeyer flask, and incubated at 28° C. on a rotary shaker at 250 RPM for 18–24 hours. Next, 10 ml volumes of the culture were inoculated into each of two 1000 ml Erlenmeyer flasks containing 100 ml of EMS-2 medium, plus 0.04% yeast extract. These were incubated at 28° C. on a rotary shaker at 250 rpm for 18 to 24 hours. The culture contents of both flasks were combined and 150 ml of the culture was used to seed 3000 ml of EMS-2 medium, plus 0.04% yeast extract, contained in a 7.5 liter fermenter (New Brunswick Model MF-107).

gram xanthan/gram cells per hour. When yeast extract concentration was reduced to 0.02%, specific productivity was adversely affected and decreased to an average of 0.23 gm xanthan/gm cells/hr. When the yeast extract concentration was restored to 0.04% again, the specific productivity came back to 0.25 gram xanthan/gram cells/hour. This shows that 0.04% yeast extract is optimum for this particular strain, and when deprived of yeast extract under conditions where it is present initially, the culture is adversely affected but improves upon restoration of the yeast extract to original levels. The data obtained in this run are given in Table XII below and demonstrate that *Xanthomonas campestris* XCP-19 ATCC 31601 is stable at high specific productivities under conditions where the parent would degenerate and exhibit lower specific productivity.

TABLE XII

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 0–325 | 2.3–2.55 | .71–.87 | 1970–2570 | .57–.64 | 0.253 | .07–.083 | 0–23.9 |
| | reduced YE to 0.04% | | | | | | |
| 325–509 | 2.08–2.19 | .58–.79 | 1345–2347 | .48–.64 | 0.23 | .078–.085 | 27.9–39.9 |
| | restored YE to 0.04% | | | | | | |
| 509–720 | 2.09–2.29 | .63–.72 | 1490–1735 | .50–.58 | 0.25 | .078–.082 | 39.9–56.1 |

EXAMPLE III

In this example, *Xanthomonas campestris* XCP-19 ATCC 31601 was grown in continuous culture in the same minimal medium as employed in Example II, EMS-2, but without yeast extract.

Inoculation procedures were the same as in Example II except that the 50 ml and 100 ml cultures were grown in the EMS-2 medium mentioned immediately above. The fermentation was inoculated and the culture was grown in a batch mode under operating conditions identical to those in Example II. Batch growth proceeded only very slowly for the first 44 hours. At that point, the concentration of iron and trace elements (Zn, Cu, Mn, Mo, B, I) was doubled in the fermenter. Over the next six hours, growth was more rapid and the cell concentration reached about 1.5 gm/liter. Continuous operation was started at a dilution rate of 0.046 hr$^{-1}$ again under operating conditions identical to those in Example II. This run lasted 1,216 hours for a total of 92 culture turnovers. A very high specific productivity of 0.3 to 0.33 gm xanthan/gm cells/hr was maintained for 386 hours during part of the run. At no time was the specific productivity less than 0.22. The results for this particular run are given in Table XIII.

TABLE XIII

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate ($hr^{-1}$) | Total Culture Turnovers |
|---|---|---|---|---|---|---|---|
| | (2X conc'n of TM, Fe)* | | | | | | |
| 0–152 | 1.96 | 0.82 | 2180 | 0.43 | 0.22 | 0.05 | 0–8.2 |
| | (1X conc'n of TM, Fe) | | | | | | |
| 152–338 | 1.98 | 0.89 | 2535 | 0.49 | 0.25 | 0.055 | 8.2–18.8 |
| | (2X conc'n of TM, Fe) | | | | | | |
| 338–505 | 2.0 | 0.72 | 1680 | 0.59 | 0.30 | 0.08 | 16.8–32.6 |
| 505–646 | 1.92 | 0.67 | 1630 | 0.59 | 0.31 | 0.087 | 32.6–43.9 |
| 646–724 | 1.97 | 0.65 | 1400 | 0.64 | 0.33 | 0.10 | 43.9–51.3 |
| | (3X conc'n of TM, Fe) | | | | | | |
| 724–817 | 1.95 | 0.53 | 980 | 0.51 | 0.26 | 0.10 | 51.3–61.3 |
| 817–913 | 2.07 | 0.67 | 1430 | 0.55 | 0.27 | 0.082 | 61.3–69.2 |
| | (2X conc'n of TM, Fe) | | | | | | |
| 913–1117 | 1.93 | 0.60 | 1170 | 0.48 | 0.25 | 0.08 | 69.2–84.5 |
| 1117–1216 | 1.87 | 0.55 | 1000 | 0.45 | 0.24 | 0.08 | 84.5–92.6 |

*The concentrations of trace elements (TM = Zn, Cu, Mn, Mo, B, I) and Fe were altered periodically between single-strength (1X) as shown above and 2X and 3X.

It will be apparent from the foregoing description that by the use of the above-mentioned novel strain it is now possible to design and operate a long-term continuous culture process for xanthan production in which the culture does not degrade, cheap simple media are used, and xanthan can be produced at a high specific productivity, thus lowering the overall economics of the process.

We claim:

1. A method for the production of a heteropolysaccharide which comprises continuously culturing a degenerative resistant strain of bacteria designated *Xanthomonas campestris* XCP-19, having the identifying characteristics of ATCC 31601, in an aqueous nutrient comprising essentially assimilable sources of carbon, nitrogen and inorganic substances wherein said medium is continuously fed to a fermentation zone to produce said polysaccharide, and withdrawing the resulting fermented medium from said zone.

2. The method of claim 1 in which said medium is a minimal medium.

3. The method of claim 2 wherein said minimal medium also contains as a complex nitrogen source, one of the group consisting of yeast extract and yeast autolysate.

4. The method of claim 1 in which the fermentation is conducted at a specific xanthan productivity in excess of 0.2 gm xanthan/gm cells/hour.

5. The method of claim 1 wherein said fermented medium is withdrawn from said zone at a rate such that an essentially steady state condition is maintained in said zone.

6. A method for the production of a heteropolysaccharide which comprises continuously culturing a degenerative resistant strain of *Xanthomonas campestris* XCP-19 having the identifying characteristics of ATCC 31601 in a minimal medium containing a growth limiting nutrient and wherein said medium is continuously fed to a first fermentation zone to produce additional amounts of said strain together with said heteropolysaccharide, thereafter transferring the effluent from said first zone to a second fermentation zone, and adding a fermentable sugar to said effluent in said second zone whereby the formation of heteropolysaccharide in said second zone is maximized.

7. The method of claim 6 in which the fermentable sugar employed is glucose.

8. The method of claims 1 or 6 in which the heteropolysaccharide is xanthan.

9. A biologically pure culture of a novel strain of *Xanthomonas campestris* XCP-19 having the identifying characteristics of ATCC 31601, said strain being capable of producing xanthan gum in recoverable amounts upon fermentation of an aqueous nutrient medium containing assimilable sources of carbon, nitrogen and inorganic substances and being resistant to cell degeneration when subjected to continuous fermentation conditions.

10. A biologically pure culture consisting essentially of *Xanthomonas campestris* XCP-19 ATCC 31601.

11. A biologically pure culture consisting essentially of *Xanthomonas campestris* XCP-19 ATCC 31601, said culture being degenerative resistant when continuously cultured in an aqueous nutrient medium, and capable of producing xanthan gum in good yields.

12. A bacterial culture consisting essentially of *Xanthomonas campestris* XCP-19 ATCC 31601.

13. A bacterial culture consisting essentially of *Xanthomonas campestris* XCP-19 ATCC 31601, said culture being degenerative resistant when continuously cultured in an aqueous nutrient medium, and capable of producing xanthan gum in good yields.

14. A bacterial culture consisting essentially of *Xanthomonas campestris* XCP-19 ATCC 31601, said culture capable of producing xanthan gum in recoverable amounts upon fermentation of an aqueous nutrient medium containing assimilable sources of carbon, nitrogen, and inorganic substances.

* * * * *